United States Patent
Gazdag et al.

(10) Patent No.: US 7,767,847 B2
(45) Date of Patent: Aug. 3, 2010

(54) PROCESS FOR THE PREPARATION OF CHIRALLY PURE N-(TRANS-4-IS)

(75) Inventors: Maria Gazdag, Budapest (HU); Tibor Gizur, Budapest (HU); Bela Hegedus, Budapest (HU); Attila Szemzo, Budapest (HU); Gabor Tarkanyi, Budaörs (HU); Jozsef Törley, Budapest (HU); Monika Babjak, Budapest (HU)

(73) Assignee: Richter Gedeon Vegyeszeti Gyar RT., Budapest (HU)

( * ) Notice: Subject to any disclaimer, the term of this patent is extended or adjusted under 35 U.S.C. 154(b) by 988 days.

(21) Appl. No.: 10/564,017

(22) PCT Filed: Jul. 8, 2004

(86) PCT No.: PCT/HU2004/000073

§ 371 (c)(1), (2), (4) Date: May 15, 2006

(87) PCT Pub. No.: WO2005/005373

PCT Pub. Date: Jan. 20, 2005

(65) Prior Publication Data
US 2007/0043117 A1 Feb. 22, 2007

(30) Foreign Application Priority Data
Jul. 10, 2003 (HU) ................. P 0302174

(51) Int. Cl.
*C07C 229/00* (2006.01)
(52) U.S. Cl. ................................ 562/450
(58) Field of Classification Search ............... None
See application file for complete search history.

(56) References Cited

U.S. PATENT DOCUMENTS

| | | | | |
|---|---|---|---|---|
| 4,816,484 A | 3/1989 | Toyoshima et al. | ......... | 514/563 |
| 5,488,150 A | 1/1996 | Sumikawa et al. | .......... | 562/450 |
| 6,861,553 B2 | 3/2005 | Yahalomi et al. | ........... | 562/450 |
| 7,148,376 B2 | 12/2006 | Yahalomi et al. | ........... | 562/450 |
| 7,314,955 B2 | 1/2008 | Rajamahendra et al. | ..... | 562/450 |
| 7,534,913 B2 * | 5/2009 | Frenkel et al. | ............... | 562/450 |
| 2004/0777725 | 4/2004 | Reguri | ........................ | 514/563 |

(Continued)

FOREIGN PATENT DOCUMENTS

EP 1535900 12/2006

(Continued)

OTHER PUBLICATIONS

"N-(Cyclohexylcarbonyl)-D-phenilamines and related compounds . . . " by H. Shinkai et al. (Am. Chem. Soc., 1989).

*Primary Examiner*—Karl J Puttlitz
(74) *Attorney, Agent, or Firm*—Jonathan Myers; Andrew Wilford

(57) ABSTRACT

The invention relates to N-(trans-4-isopropylcyclohexylcarbonyl)-D-phenylalanine (nateglinide) in the novel crystalline form "G" and a process for the preparation thereof. A process for the preparation of chirally pure nateglinide by treating a lower alkyl ester thereof with a base to yield an alkali salt and liberating the product from said salt by proper addition of an acid, is also provided. Still another aspect of the invention is a process for the preparation of nateglinide in the crystalline form "H" from other crystalline modifications of nateglinide.

4 Claims, 4 Drawing Sheets

U.S. PATENT DOCUMENTS

Figure 1:
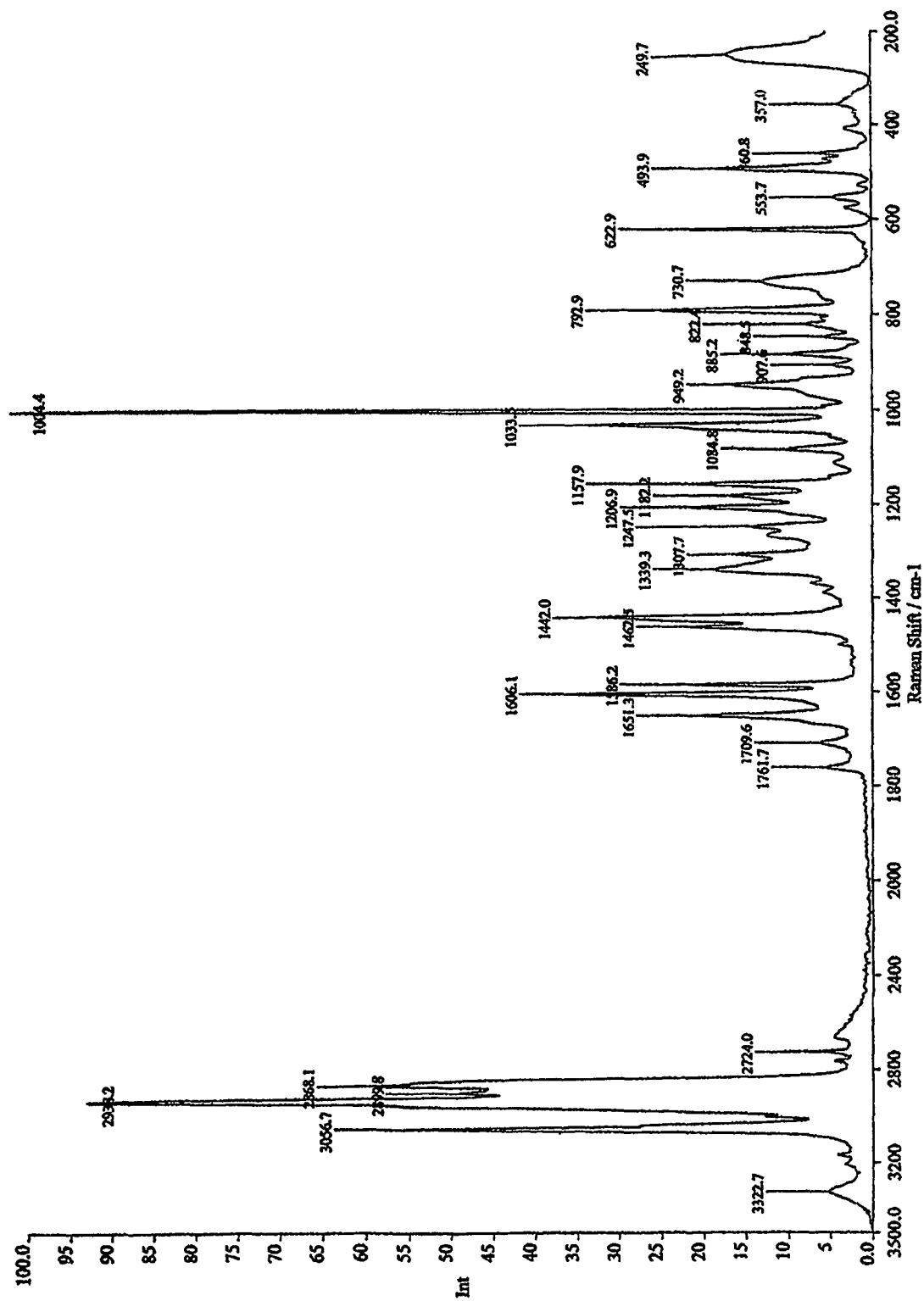

| | | | |
|---|---|---|---|
| 2004/0116526 A1* | 6/2004 | Yahalomi et al. | 514/563 |
| 2004/0181089 A1* | 9/2004 | Yahalomi et al. | 562/450 |
| 2005/0014949 A1* | 1/2005 | Yahalomi et al. | 546/270.4 |
| 2005/0075400 A1* | 4/2005 | Yahalomi et al. | 514/563 |
| 2005/0090552 A1 | 4/2005 | Yahalomi et al. | 514/563 |
| 2005/0101672 A1 | 5/2005 | Koguchi et al. | 514/563 |
| 2005/0165108 A1 | 7/2005 | Rajmahendra et al. | 514/563 |
| 2005/0234129 A1 | 10/2005 | Sutton et al. | 514/563 |
| 2005/0256336 A1 | 11/2005 | Sutton | 562/450 |
| 2006/0004102 A1 | 1/2006 | Wizel et al. | 514/563 |
| 2007/0043117 A1 | 2/2007 | Gazdag et al. | 514/563 |
| 2007/0167523 A1 | 7/2007 | Takahashi et al. | 514/563 |
| 2008/0081927 A1 | 4/2008 | Sutton | 562/442 |
| 2008/0194867 A1 | 8/2008 | Koguchi et al. | 562/450 |
| 2008/0319222 A1 | 12/2008 | Sutton | 562/450 |
| 2009/0143469 A1 | 6/2009 | Sutton et al. | 514/563 |

FOREIGN PATENT DOCUMENTS

| | | |
|---|---|---|
| WO | WO 2004018408 | 3/2004 |
| WO | WO 2007113650 | 10/2007 |
| WO | WO 2007135533 | 11/2007 |
| WO | WO 2008096373 | 8/2008 |

* cited by examiner

PROCESS FOR THE PREPARATION OF CHIRALLY PURE N-(TRANS-4-IS)

CROSS REFERENCE TO RELATED APPLICATIONS

This application is the US national phase of PCT application PCT/HU2004/000073 filed 8 Jul. 2004 with a claim to the priority of Hungarian patent application P0302174 itself filed 10 Jul. 2003.

The invention relates to N-(trans-4-isopropylcyclohexylcarbonyl)-D-phenylalanine (nateglinide) of the formula (I) in the crystalline form "G", as well as a process for the preparation thereof. Another aspect of the invention is a process for the preparation of nateglinide in crystalline form "H" from other crystal modifications having lower melting points. Further the invention provides a process for preparing chirally pure nateglinide

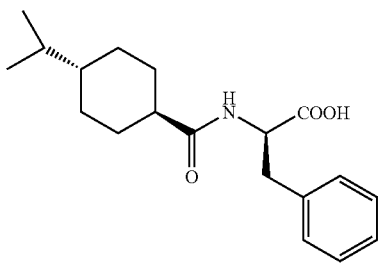

(I)

from a compound of the general formula (II),

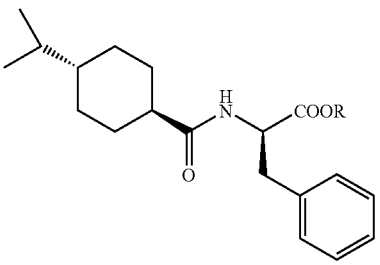

(II)

wherein R is a lower alkyl ($C_1$-$C_4$) group or hydrogen, which comprises treating the compound of the general formula (II) with a base to yield an alkali salt, then adding an acid in a proper manner to said alkali salt to liberate the product.

Nateglinide is known as the active ingredient of a composition for treating type 2 diabetes (J. Med. Chem. 32, 1436 (1989)). Also known are the methods for the preparation of the product and two crystalline forms thereof (the instable form "B", mp: 127-129° C. and the stable form "H", mp: 139° C.).

In J. Med. Chem. (ibid) preparation of the crystalline form "B" is described; in the reaction this product is formed in each case.

In U.S. Pat. No. 5,488,150 patent preparation of the crystalline form "H" from the instable crystal modification "B" is disclosed. This rearrangement occurs when modification "B" is kept in an aqueous organic solvent (acetone, acetonitrile or alcohols) under stirring for 24 hours. This process however, has the drawback that the stable modification "H" which is contained in the composition is prepared in a time-consuming additional step. Another disadvantage is that the modification "B" is difficult-to-filter which is a serious problem in an industrial process. Still another drawback is that application of an aqueous system makes recovery of the organic solvent difficult.

According to J. Med. Chem. (ibid) and U.S. Pat. No. 4,816,484 patent specification the product is obtained by alkaline hydrolysis of the nateglinide methyl ester yielding the corresponding alkali salt, which is turn, is treated with mineral acid to give the product. While none of the aforesaid publications makes mention of the optical purity of the product, it can be of fundamental importance in view of the difference in the biological activity of the enantiomers. Therefore, every effort should be taken to minimize the amount of enantiomeric impurity.

It is known from the chemical literature that the chiral carbon atom present in the α-amino acids and dipeptides is more or less susceptible to racemization. This susceptibility is so expressed that even in the presence of a weak base, such as barium hydroxide (Hoppe-Syler's Z. Physiol. Chem. 33, 173 (1901)) or calcium hydroxide racemization takes place resulting in enantiomeric contamination in the nateglinide end-product.

Reproducing the process described in the U.S. Pat. No. 4,816,484 we have measured 0.2-0.3% enantiomeric impurity in the product; this value doesn't meet the tight requirements imposed either by the pharmacopoeia or the health authorities and quality directives, since the acceptable maximum for chiral impurities is 0.1%. Consequently the product prepared by the process mentioned above needs further purification, which could be done by several recrystallization steps from very thin solutions with a rather low (10-20%) yield.

Another possible purification method is to use a chiral reagent in a calculated amount based on the enantiomeric impurity. This latter method, however, is not profitable on industrial scale since it results in a substantial increase in costs and processing time.

The aim of the present invention is to provide a process suitable for plant-scale preparation of chirally pure nateglinide with high yield and short reaction time in the crystalline form "H" required for the pharmaceutical composition or to obtain crystalline form "H" from other crystal modifications.

During our experiments we have surprisingly found that when the nateglinide is liberated from a salt thereof in the presence of a water-miscible organic solvent at a temperature below 20° C., a crystalline modification not known in the art is obtained with an mp of 100-109° C. and with filtration properties which are better than those of the known crystalline modifications. We designate this novel form crystalline modification "G".

From the above modification "G" the crystalline form "H" is obtained on heating in an alkane or cycloalkane, such as n-hexane or n-heptane without using any aqueous organic solvent.

Further we have quite unexpectedly found that when the product liberation either from an alkali salt obtained at the end of the alkaline hydrolysis of the nateglinide alkyl ester, or from an alkali salt of nateglinide containing enantiomeric impurity, is not carried out in a one-step fashion by adding equivalent amount of a mineral acid, but the acid is added in two portions in such a way that first less than equimolar amount of the acid is added yielding a mixture of nateglinide and an alkali salt thereof, isolating said mixture and adding further amount of mineral acid to it, the nateglinide so obtained is chirally pure, i.e. contains no enantiomeric impurity. When nateglinide is prepared from a salt thereof different crystalline modifications can be obtained depending on the reaction temperature.

It is really surprising that by adding mineral acid to the solution of an alkali salt of a substance it is not the acidic product which is obtained in an amount equivalent to the reagent but an acid-salt-mixture. Also is surprising that by reacting a nateglinide salt containing enantiomeric impurity with an achiral acid, a pure product containing no enantiomeric impurity is obtained without adding any chiral reagent/auxiliary.

This process makes avoidable to crystallize the product repeatadly from very thin solutions, an operation demanding cost and labour and not even certain at chiral purity.

In our experiments we accomplished also the purification of the nateglinide containing enantiomeric impurity in such a manner that to the product containing the enantiomeric impurity a base is added to form the corresponding salt, and the product liberation from said salt is not done in one-step by adding a mineral acid in equivalent amount, but by adding the acid in two portions in such a way that first less than equimolar amount of the acid is added yielding a mixture of nateglinid and an alkali salt thereof, said mixture is isolated and a further amount of the mineral acid is added to it to give the chirally pure nateglinide.

Accordingly the invention provides a process for the preparation of crystalline modifications of nateglinide of the formula (I), by treating a compound of the general formula (II) with a base to yield an alkali salt of the product and liberating the product from said salt, in such a manner that the liberation of the product by an acid is carried out below room temperature, preferably within the temperature range of 0° C. to 20° C. to yield nateglinide in crystalline modification "G"; or above room temperature, preferably within the temperature range of 65° C. to 70° C. to yield nateglinide in crystalline modification "H". Nateglinide in the crystalline form "G"—a modification not known in the art—is also within the scope of the invention.

The invention also provides a process for the preparation of nateglinide of the formula (I), by treating a compound of the general formula (II) with a base to yield an alkali salt of the product and liberating the product from said salt, in such a manner that the liberation of he product is carried out by addition of equivalent amount of a mineral acid in portions, preferably in two portions (selective precipitation), i.e. first less than equimolar amount of the acid is added yielding a mixture of nateglinid and an alkali salt thereof, said mixture is isolated and a further amount of the mineral acid is added to it to give the chirally pure nateglinide.

Further, the invention provides a process for the preparation of the stable crystalline form "H" from other crystalline modifications having lower melting points.

According to one embodiment of the invention nateglinide methyl ester is hydrolysed in an aqueous alkanol at 15-30° C. in the presence of 1-1.5 equivalent, preferably 1.2 equivalent of sodium hydroxide. The solution containing the alkali salt obtained is treated with a mineral acid the first time in an amount calculating with 0.4-0.6 equivalent of the ester plus the excess base. The mixture of nateglinide and alkali salt thereof so obtained is isolated by filtration, the filter cake is dissolved and the solution is heated to a temperature—in the case of crystalline modification "H" to 65-70° C.—suitable for continuing the liberation of the product with aqueous mineral acid. The precipitated product is isolated by filtration and dried at 50-60° C.

When the crystalline modification "G" not known in the art is prepared, liberation of the product is accomplished below 20° C. and the product is dried at 30-35° C. In the case of crystalline modification "B" described in the literature, acidifying is carried out at 30-35° C. and the product is dried at 40-45° C.

Rearrangement of the crystalline modifications having lower melting points into the stable crystalline modification "H" is carried out without employing aqueous solvents; it is accomplished in alkanes or cycloalkanes, such as n-hexane or n-heptane with short term boiling.

The base employed in the process may be an alkali hydroxide; preferably sodium hydroxide, potassium hydroxide or lithium hydroxide; most preferably it is sodium hydroxide.

The mineral acid employed in the process can be hydrochlorid acid, sulphuric acid; preferably it is hydrochloric acid.

The product containing chiral impurity is purified by adding equivalent amount of an alkali hydroxide to it in methanolic solution, followed by the selective precipitation described above.

Chiral purity of the product obtained according to the invention can readily and exactly be determined by HPLC and NMR spectroscopy.

When the end-product obtained according to our method is dissolved in a suitable solvent mixture ($CCl_4$:$CD_2Cl_2$=5:7 v/v) and its NMR spectrum is obtained under the conditions given below, the ratio of enantiomers in the end-product can be determined without the use of any external chiral auxiliary; evaluation is simply based on distinct $^1$H-NMR signals brought about by self-recognition of the enantiomers.

The process according to the invention has the advantage that chirally pure product can be prepared in a simple way with good yield without making several purification steps and any of the crystalline modifications can be obtained; further, by carrying out the product liberation at a suitable temperature, crystalline modification "G" which is easy-to-filter can also be obtained. Since for the preparation of crystalline modification "H" from other crystalline forms having lower melting points a solvent other than a mixture of aqueous and organic solvent is used, recovery of the organic solvent can easily be accomplished, which again, is an advantage.

Attached are four figures showing certain spectra of the different crystalline modifications; namely In FIG. 1. Raman spectrum of the nateglinide crystalline modification "G" of the invention is shown.

Figure 2:
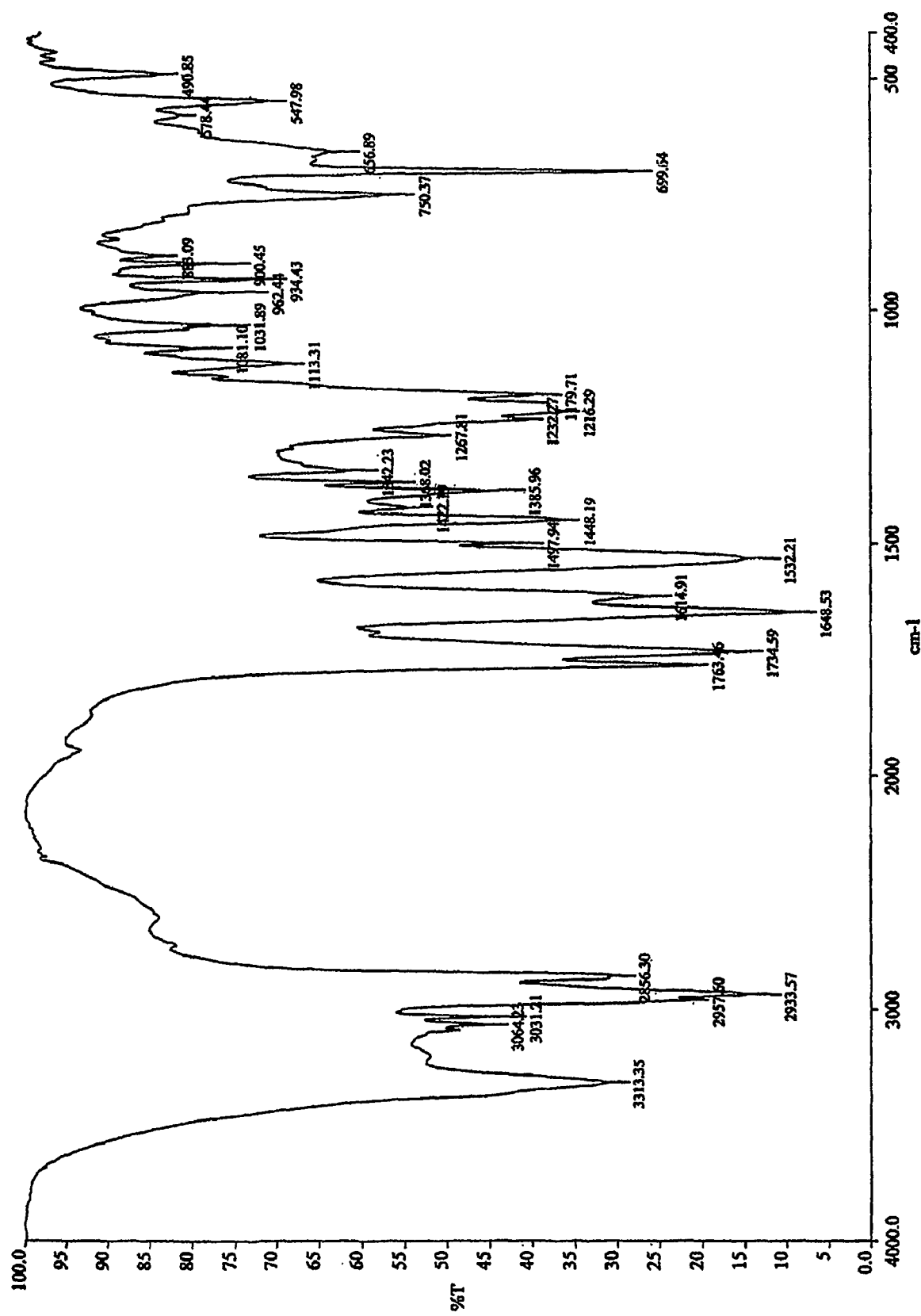

In FIG. 2. infra-red spectrum of the nateglinide crystalline modification "G" of the invention is shown.

Figure 3:
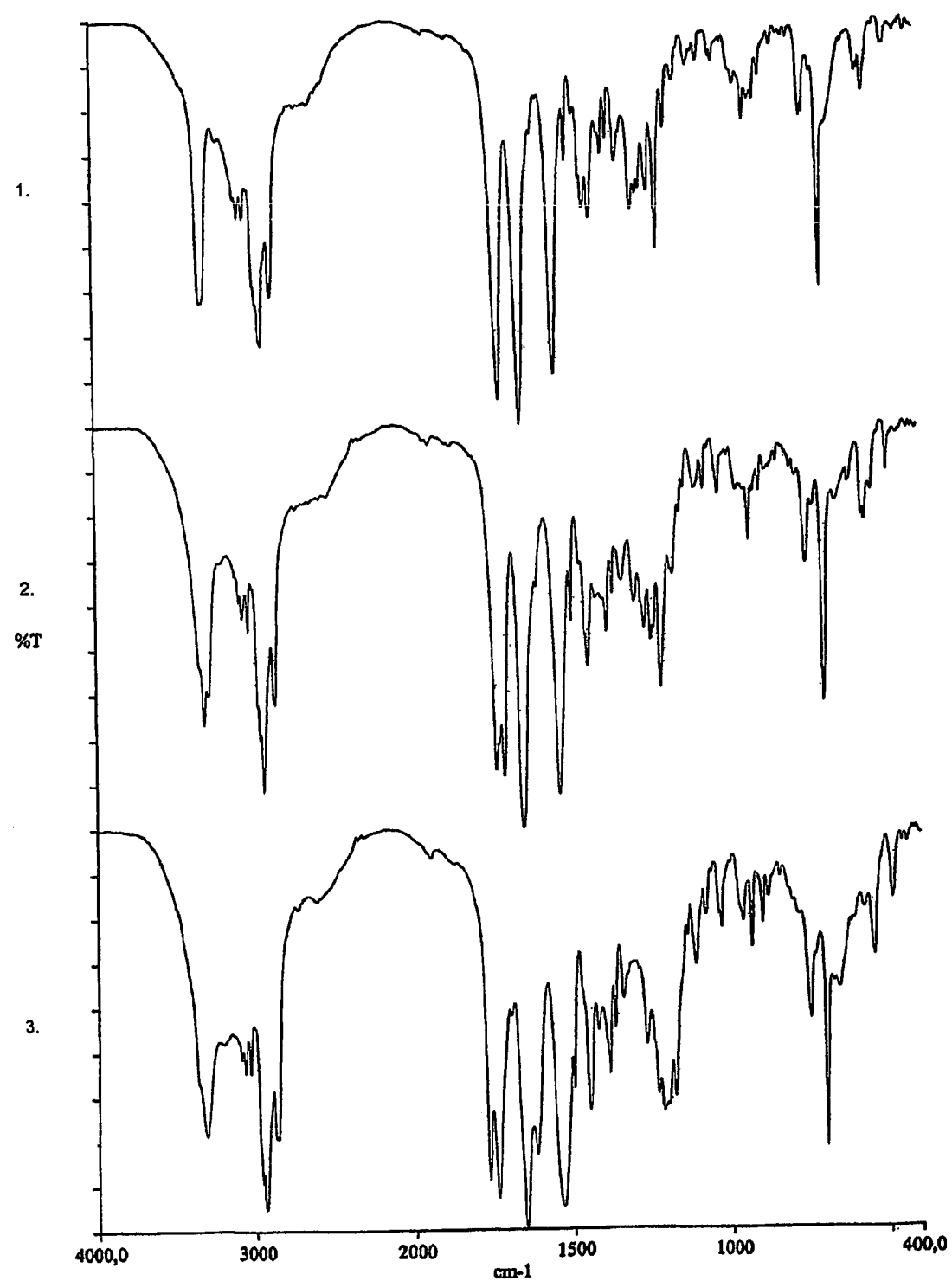

In FIG. 3. infra-red spectra of the nateglinide crystalline modification "H", "B" and "G" are given designated as 1, 2 and 3, respectively.

Figure 4:
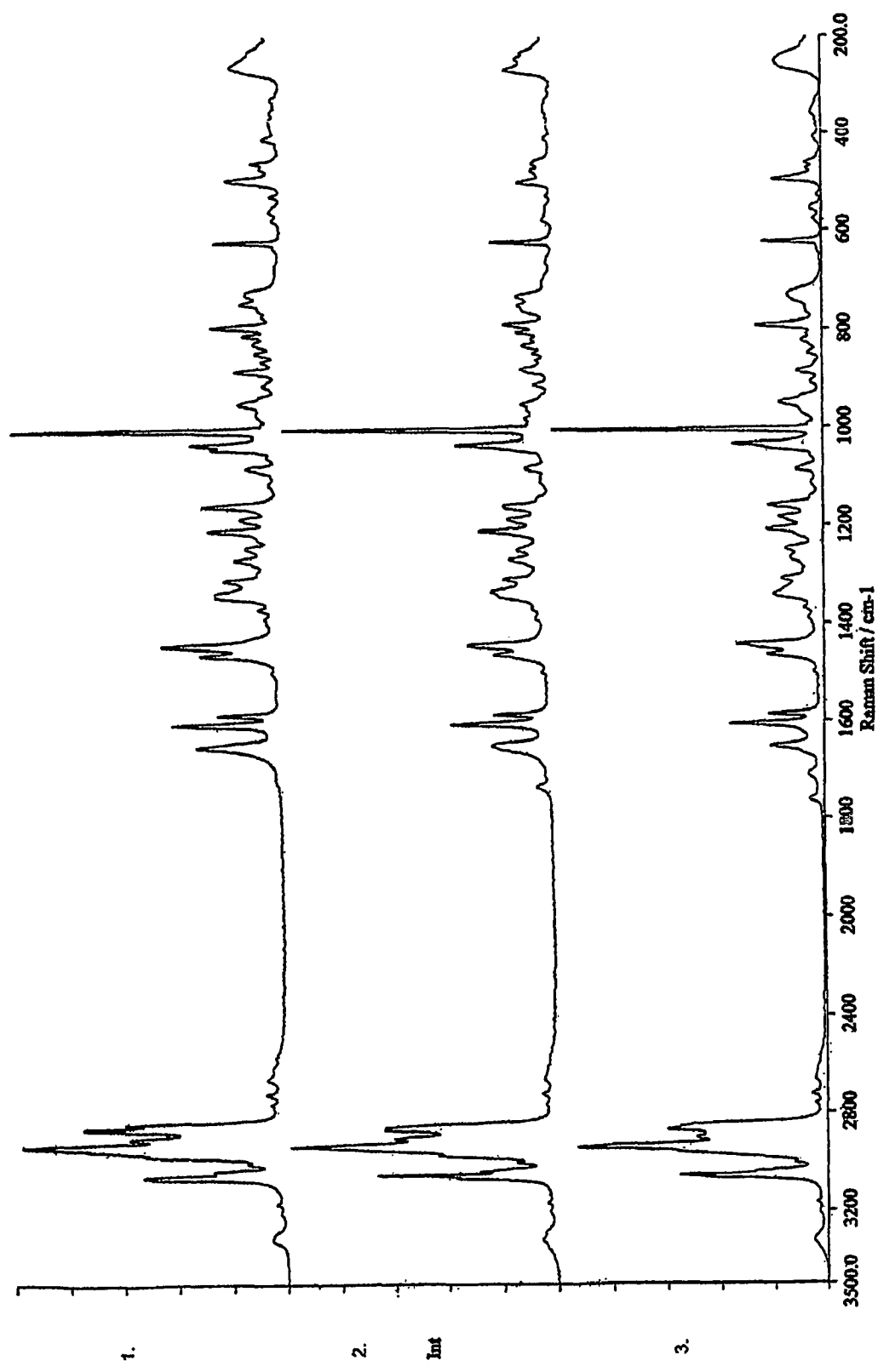

In FIG. 4. Raman spectra of the nateglinide crystalline modification "H", "B" and "G" are given designated as 1, 2 and 3, respectively.

Spectroscopic data of the individual modifications are set out below ($cm^{-1}$) with the intensive bands underlined.

Nateglinide Modification "H":

IR: 3315, 3065, 3031 <u>2926</u>, 2861, 1714, 1650, 1541, 1446, <u>1425</u>, 1292, <u>1214</u>, <u>1187</u>, 934, 756, 742, 700, 558

Raman: 3059, 2935, 2902, 2862, <u>2844</u>, 1652, 1606, 1587, 1463, 1443, 1337, 1310, 1208, 1158, 1080, 1004, 950, 884, <u>828</u>, <u>811</u>, 794, 748, 623, 494, 408, 263

Nateglinide Modification "B":

IR: 3313, 3064, 3028, 2934, 2858, 1732, <u>1706</u>, 1648, <u>1536</u>, 1446, 1386, <u>1298</u>, <u>1217</u>, 1178, 1078, 934, 755, 702, <u>569</u>, <u>498</u>

Raman: 3055, <u>3040</u>, 2936, 2903, 2866, <u>1735</u>, 1650, 1606, 1586, 1462, 1442, <u>1333</u>, 1209, 1158, 1081, 1004, 911, <u>880</u>, 832, <u>805</u>, 750, 732, 623, <u>577</u>, 499, 474, 268

Nateglinide Modification "G":

IR: 3313, 3064, 3031, 2934, 2856, 1763, 1735, 1648, 1614, 1533, 1448, 1386, 1368, 1216, 1180, 1113, 1081, 934, 750, 700, 574, 491

Raman: 3057, 2938, 2868, 1762, 1710, 1651, 1606, 1586, 1462, 1442, 1339, 1207, 1182, 1158, 1085, 1004, 949, 885, 822, 793

HPLC conditions for determination of chiral purity:

Column: CHIRALCEL OD-RH 150×4.6 mm, 5 µl

Eluent: 0.1 M K-hexafluoro-phosphate buffer: methanol=30:70

Flow rate: 0.3 ml/min

Temperature: 40° C.

Detection: 214 nm

Injected volume: 20 µl

Sampling: 1 mg of the product to be tested is dissolved in 5 ml eluent.

Ratio of the enantiomers is measured by 1H-NMR spectroscopy under the conditions set out below:

Working frequency: 500 MHz

Solvent: $CCl_4:CD_2Cl_2$=7:5 v/v

Reference: $\delta_{CD2Cl2}$=5.32 ppm

Temperature: 21.5° C.

22 mg of the end-product were dissolved in the above solvent. 0.7 ml aliquot of the solution was used without filtration for analysis. At 4.8 ppm CW coupling with 10 decibel was employed. From the group of signals in the 3.08-3.17 ppm range the enantiomer ratio is determined by the deconvolution method.

The invention is further illustrated by the following non-limiting examples.

EXAMPLE 1

Preparation of Chirally Pure Nateglinide in the Crystalline Modification "G"

Into a four-necked 1 l flask equipped with a swinging blade stirrer, a condenser, a thermometer and a feeding funnel 200 g (250 ml) of methanol and 33.1 g (0.1 mol) of nateglinide methyl ester were added. To the suspension formed 4.8 g (0.12 mol) sodium hydroxide dissolved in 110 ml of water were added dropwise at 20-25° C. while the mixture is cooled with cold water. The reaction mixture was kept at 20-25° C. with stirring for 4 hours causing the suspension to become a solution. After the ester was used up in the reaction the small amount of solids was removed from the solution by filtration. To the filtrate 6.9 g (5.85 ml; 0.07 mol) of concentrated hydrochloric acid in 5.5 ml of water were dropwise added at 10-15° C. The thick suspension obtained was stirred at 13-18° C. for 30 minutes and then filtered. The filter cake was washed first with 43 g (50 ml) of methanol/water mixture (2:1 v/v; 26.3 g methanol+16.7 g water) then with 200 ml of water. The wet substance was dissolved in 514 g (650 ml) of methanol at 25-30° C., the solution was then cooled to 15-20° C. and 5.5 g (4.7 ml; 0.056 mol) of concentrated hydrochloric acid in 5 ml of water were added so that after the addition the pH of the solution would be between 2 and 3. After further stirring for 10 minutes water of 5° C. temperature was added (750 ml) and the precipitate obtained was stirred for 20 minutes. The product was filtered off, washed with water (200 ml) and dried under infra-red lamp at 30-35° C., yielding 26.3 g (94.4%) of nateglinide in the crystalline modification "G".

Mp: 100-109° C.

Enantiomeric impurity was under the detection limit of HPLC; total amount of other impurities was below 0.1%.

EXAMPLE 2

Preparation of Chirally Pure Nateglinide in the Crystalline Modification "H"

Into a four-necked 1 l flask equipped with a swinging blade stirrer, a condenser, a thermometer and a feeding funnel 200 g (250 ml) of methanol and 33.1 g (0.1 mol) of nateglinide methyl ester were added. To the suspension formed 4.8 g (0.12 mol) sodium hydroxide dissolved in 110 ml of water were added dropwise at 20-25° C. while the mixture is cooled with cold water. The reaction mixture was kept at 20-25° C. with stirring for 4 hours causing the suspension to become a solution. After the ester was used up in the reaction the small amount of solids was removed from the solution by filtration. To the filtrate 6.9 g (5.85 ml; 0.07 mol) of concentrated hydrochloric acid in 5.5 ml of water were dropwise added at 10-15° C. The thick suspension obtained was stirred at 13-18° C. for 30 minutes and then filtered. The filter cake was washed first with 43 g (50 ml) of methanol/water mixture (2:1 v/v; 26.3 g methanol+16.7 g water) then with 200 ml of water. The wet substance was dissolved in 514 g (650 ml) of methanol at 50-60° C. and at the same temperature 5.5 g (4.7 ml; 0.056 mol) of concentrated hydrochloric acid in 5 ml of water were added so that after the addition the pH of the solution would be between 2 and 3. After further stirring for 10 minutes water was added (750 ml) at the above temperature and the precipitate obtained was stirred for 20 minutes at the above temperature. The product was filtered off, washed with water (200 ml) and dried under infra-red lamp at 60-70° C., yielding 26.3 g (94.4%) of nateglinide in the crystalline form "H".

Mp=138-139° C.

Enantiomeric impurity was under the detection limit of HPLC; total amount of other impurities was below 0.1%.

EXAMPLE 3

Preparation of Chirally Pure Nateglinide in the Crystalline Modification "H" Via the Crystalline Form "G"

Into a four-necked 1 l flask equipped with a swinging blade stirrer, a condenser, a thermometer and a feeding funnel 200 g (250 ml) of methanol and 33.1 g (0.1 mol) of nateglinide methyl ester were added. To the suspension formed 4.8 g (0.12 mol) sodium hydroxide dissolved in 110 ml of water were added dropwise at 20-25° C. while the mixture is cooled with cold water. The reaction mixture was kept at 20-25° C. with stirring for 4 hours causing the suspension to become a solution. After the ester was used up in the reaction the small amount of solids was removed from the solution by filtration. To the filtrate 6.9 g (5.85 ml; 0.07 mol) of concentrated hydrochloric acid in 5.5 ml of water were dropwise added at 10-15° C. The thick suspension obtained was stirred at 13-18° C. for 30 minutes and them filtered. The filter cake was washed first with 43 g (50 ml) of methanol/water mixture (2:1 v/v; 26.3 g methanol+16.7 g water) then with 200 ml of water. The wet substance was dissolved in 514 g (650 ml) of methanol at 25-30° C., the solution was then cooled to 15-20° C. and 5.5 g (4.7 ml; 0.056 mol) of concentrated hydrochloric acid in 5 ml of water were added so that after the addition the pH of the solution would be between 2 and 3. After further stirring for 10 minutes water was added (750 ml) at the above temperature and the precipitate obtained was stirred for 20 minutes. Nateglinide crystals of the "G" modification are filtered and washed with 200 ml of water.

The wet substance is transferred into a round bottom flask and was boiled in 513 g (750 ml) of n-heptane with stirring for 1.5 hours. The suspension was cooled to 20-25° C. and stirred for 20 minutes at this temperature. The product was filtered, washed with 2×100 ml (2×68 g) n-heptane and dried under infra-red lamp at 50° C., affording 25.68 g (80.9%) of nateglinide in the crystalline form "H".

Mp=139-140° C.

Enantiomeric impurity was under the detection limit of HPLC; total amount of other impurities was below 0.1%.

EXAMPLE 4

Purification of Nateglinide Containing Enantiomeric Impurity 6.34 g (0.02 mol) of nateglinide (chiral purity: 98%) were dissolved in 50 ml of methanol. To the solution 0.8 g (0.02 mol) of sodium hydroxide in 22 ml of water were added. To this solution a mixture of 0.83 ml concentrated hydrochloric acid and 1 ml water were added dropwise at 10-15° C. temperature. After 30 minutes of stirring the precipitate was filtered, washed with a mixture of methanol/water 2:1, v/v (25 ml) followed by 50 ml of water. The wet substance was dissolved in methanol (130 ml) and a mixture of 0.83 ml concentrated hydrochloric acid and 1 ml water were added. The mixture was stirred for 10 minutes, 150 ml of water were added and stirring was continued for 20 minutes. The product was filtered, washed, suspended in n-heptane (100 ml) and boiled for 1.5 hours. After cooling the product was filtered and dried at 50° C. giving 4.2 g (66.4%) of nateglinide.

Mp=138-139° C.

Enantiomeric impurity was under the detection limit of HPLC; total amount of other impurities was below 0.1%.

The invention claimed is:

1. Crystals of nateglinide in the "G" form, having
(a) a melting point of 100 to 109° C.;
(b) an infra-red spectrum with intensive bands at 1763, 1735, 1614, 1533, 1180, 750, 574 and 491 cm-1; and
©) a Raman spectrum with intensive bands at 1762, 1710, 1182 and 822 cm-1.

2. A process for the preparation of crystalline modification "G" of N-(trans-4-isopropylcyclohexyl carbonyl)-D-phenylalanine (nateglinide) of the formula (I) and having the melting point, infra-red spectrum and Raman spectrum of claim 1

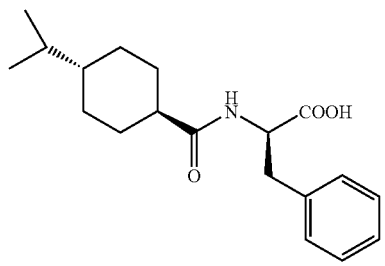

which comprises the steps of:
(a) treating a compound of the general formula

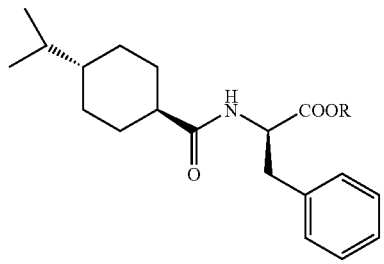

wherein R is a lower (C1-C4) alkyl group or hydrogen, with a base at 20 to 25° C. to yield an alkali salt, and
(b) liberating the product of the Formula (I) from the acid salt with an acid, by acidifying the alkali salt in a temperature range of 10 to 15° C. with a first portion of acid to form a suspension, which is then stirred at 13 to 18° C. for 30 minutes, filtered to form a filter cake, washing the filter cake with a methanol/water mixture and then water, dissolving the filter cake in methanol at 25 to 30° C. to form a solution, cooling the solution to 15° C., and again acidifying the solution so that after acidifying the solution again, the pH of the solution is 2 to 3, stirring the solution and adding water at a temperature of 5° C. to the solution to obtain a precipitate, and drying the precipitate at 30 to 35° C. to obtain the desired product.

3. A process according to claim 2, wherein according to step (a) methanol containing 20-50% water by volume is employed as solvent.

4. A process according to claim 2 for liberation of nateglinide from the alkali salt thereof according to step (b), wherein as the first portion of the acid an amount considering the excess base plus 0.4-0.6 equivalent of the compound of the formula (II) is employed.

* * * * *